(12) United States Patent
Claereboudt et al.

(10) Patent No.: US 8,963,111 B2
(45) Date of Patent: Feb. 24, 2015

(54) SHIELDING DEVICE FOR AN IRRADIATION UNIT AND IRRADIATION METHOD

(75) Inventors: Yves Claereboudt, Nil-Saint-Vincent (BE); Thomas Colmant, Braives (BE); Michel Closset, Avin (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 13/492,100

(22) Filed: Jun. 8, 2012

(65) Prior Publication Data
US 2013/0043408 A1 Feb. 21, 2013

(30) Foreign Application Priority Data
Jun. 9, 2011 (EP) .................................... 11169380

(51) Int. Cl.
*G21K 1/02* (2006.01)
*A61N 5/10* (2006.01)
*G21K 1/10* (2006.01)

(52) U.S. Cl.
CPC ................. *G21K 1/10* (2013.01); *A61N 5/1077* (2013.01); *G21K 1/02* (2013.01); *A61N 5/1042* (2013.01);
(Continued)

(58) Field of Classification Search
CPC ............ A61N 5/10; A61N 2005/1087; A61N 2005/109; A61N 2005/1095; G21K 1/02
USPC ....................................... 250/505.1
See application file for complete search history.

(56) References Cited

U.S. PATENT DOCUMENTS

| 3,950,651 A | 4/1976 | Flocee |
| 6,080,992 A | 6/2000 | Nonaka et al. |

(Continued)

FOREIGN PATENT DOCUMENTS

| FR | 2764199 A1 | 12/1998 |
| WO | 2008106218 A2 | 9/2008 |

(Continued)

OTHER PUBLICATIONS

Pedroni et al., "The 200-MeV proton therapy project at the Paul Scherrer Institute: Conceptual design and practical realization", Med. Phys. 22(1), Jan. 1995.*

(Continued)

*Primary Examiner* — Jack Berman
*Assistant Examiner* — James Choi
(74) *Attorney, Agent, or Firm* — Fitch Even Tabin & Flannery LLP

(57) ABSTRACT

The present invention relates to a method for obtaining a shielding element for minimizing the penumbra of a beam of hadrons outside a target area, the hadron beam being guided in a longitudinal direction by an irradiation unit, and the beam having a width ($\sigma$). The method includes:
  (i) defining a closed or open contour of said target area;
  (ii) providing a block having a longitudinal thickness capable of blocking the passage of said beam and having a lateral surface perpendicular to said longitudinal thickness;
  (iii) forming an aperture of a shape similar to said contour and crossing said longitudinal thickness of said block for letting through said beam, said aperture forming a longitudinal internal surface; and
  (iv) trimming said block so as to form a longitudinal external surface around said longitudinal internals surface, said longitudinal internal and longitudinal external surfaces delimiting a side wall.

16 Claims, 8 Drawing Sheets

(52) U.S. Cl.
CPC ... *A61N 2005/1087* (2013.01); *A61N 2005/109* (2013.01); *A61N 2005/1094* (2013.01); *A61N 2005/1095* (2013.01)
USPC .................................. 250/505.1; 250/515.1

(56) References Cited

U.S. PATENT DOCUMENTS

| | | | |
|---|---|---|---|
| 6,717,162 | B1 | 4/2004 | Jongen |
| 7,826,593 | B2 | 11/2010 | Svensson et al. |
| 2009/0289192 | A1 | 11/2009 | Westerly et al. |
| 2011/0127443 | A1* | 6/2011 | Comer et al. ............. 250/396 R |

FOREIGN PATENT DOCUMENTS

| | | |
|---|---|---|
| WO | 2010019504 A1 | 2/2010 |
| WO | 2011060133 A1 | 5/2011 |

OTHER PUBLICATIONS

Delaney et al., "Proton and Charged Particle Radiotherapy", Lippincott Williams & Wilkins, (2008) p. 33-84.*

Bonnett, "Current Developments in Proton Therapy: a review", Phys. Med. Biol. 38 (1993) 1371-1392.*

Buchsbaum et al., "Supine Proton Beam Craniospinal Radiotherapy Using a Novel Tabletop Adapter", Medical Dosiometry 38 (2013) 70-76.*

Anferov et al., "Status of the Midwest Proton Radiotherapy Institute", Particle Accelerator Conference, 2003. PAC 2003. Proceedings of the.*

European Search Report, European Patent Application 11169380.0, dated Oct. 20, 2011, 5 pages (in French language).

Anferov et al., "Status of the Midwest Proton Radiotherapy Institute," Indiana University Cyclotron Facility, 3 pages (2003).

Bonnett, "Current developments in proton therapy: a review," Phys. Med. Biol. 38 (1993) 1371-1392, dated Jun. 14, 1993, 22 pages.

Buchsbaum et al., "Supine proton bean craniospinal radiotherapy using a novel tabletop adaptor," Medical Dosimetry 38 (2013) pp. 70-76, dated Jul. 23, 2012.

Delaney et al., "Proton and Charged Particle Radiotherapy," Chapters 5 and 6, 34 pages (2008).

* cited by examiner

SHIELDING DEVICE FOR AN IRRADIATION UNIT AND IRRADIATION METHOD

CROSS-REFERENCE TO RELATED APPLICATION

This application claims foreign priority under 35 U.S.C. §119 to European Patent Application No. 11169380.0, filed Jun. 9, 2011, which is hereby incorporated herein by reference in its entirety.

TECHNICAL FIELD

The present invention according to a first aspect relates to a method for obtaining a shielding element for minimizing the penumbra of a hadron beam outside a target area, said hadron beam stemming from a source and scanning said target area. According to a second aspect, the invention relates to a shielding element made according to the claimed method for obtaining it. According to a third aspect, the present invention relates to an irradiation unit. According to a fourth aspect, the present invention relates to a method for scanning a target area with a hadron beam.

DESCRIPTION OF THE STATE OF THE ART

Recent hadron therapy techniques for treating cancers give the possibility of accurately delivering a dose on a target volume, for example a tumor, while preserving the surrounding tissues. A hadron therapy apparatus comprises a particle accelerator producing a beam of charged particles, a means for conveying the beam and an irradiation unit. The irradiation unit delivers a dose distribution over the target volume and generally comprises means for controlling the delivered dose, like for example an ionization chamber, as well as means for controlling the beam, such as for example a collimator or scanning magnets depending on the delivery mode of the beam used. Two great beam delivery modes are used in hadron therapy: a first delivery mode comprises so-called passive diffusion techniques for the beam and a second more elaborate treatment mode comprises dynamic scanning techniques for the beam.

The passive diffusion methods resort to a set of elements with which the trajectory of the particles may be adjusted as far as the maximum depth point of the region to be irradiated and over the required width. In order to obtain a dose which coincides at best with the target volume, it is necessary to use a compensator and a collimator specifically made for each patient's beam. A major flaw of this technique is that neighboring tissues localized upstream and outside the target volume may also be subject to high doses from beams. Further, the manufacturing of the compensator(s) and of the collimator(s) specific to the tumor of the patient and to the irradiation angle is complicated and expensive.

Also, an irradiation unit of a hadron therapy apparatus delivering a beam according to a passive diffusion method comprises a device for attaching a compensator and a collimator which is specific to it. The attachment device allows translation along the axis of the beam so as to place the compensator and collimator as close as possible to the patient. The collimator is generally machined in a brass block with dimensions adapted to the device for attaching the collimator, regardless of the aperture of the collimator. The height of the block along the direction of the beam should be sufficient in order to prevent passage of the beam. The weight of such a collimator is relatively great, which poses manipulation problems for the therapist. Often such a collimator is divided into several portions according to its height for facilitating handling, nevertheless the weight of these collimator portions remains great and these portions require accurate alignment relatively to each other. A collimator is located at the end of the irradiation unit and at a distance close to the patient, and may have a total weight of the order of 30 kg, which imposes a sufficiently robust irradiation unit as well as a powerful displacement system in the case when gravity has to be opposed (vertical irradiation).

Other collimators exist such as for example multileaf collimators as described in documents US20090289192, WO2008106218, the aperture of which may be modified depending on the shape of the target volume. The multileaf collimators are used for passive diffusion techniques and require leaves which have to be long in order to cover the whole of the surface of the produced scattered beam regardless of the required aperture of the collimator and should be thick so as to stop the totality of the beam. Because of these two needs, such multileaf collimators have disadvantages in terms of weight and bulkiness of the irradiation unit.

In a second mode for delivering a beam using dynamic techniques for scanning the beam, such as for example the <<PBS>> (for Pencil Beam Scanning) technique described in document EP1 147 693, a thin beam of particles oriented along an axis z is scanned along a plane orthogonal to this axis z over the target volume by means of scanning magnets. By varying the energy of the particle beam, different layers in the target volume may be successively irradiated. In this way, the radiation dose may be delivered over the entirety of the target volume. <<PBS>> techniques allow irradiation of a target volume without having to either resort to a collimator, or to an energy compensator specific to the patient.

The distribution of the particles of the thin beam at the output of the irradiation unit follows a Gaussian distribution. The width $\sigma$ of the hadron beam at the output of the irradiation unit increases when the energy decreases because the scattering of the beam in the materials crossed (detectors, air, . . . ) before exiting the irradiation unit varies with the beam energy. For high energy beams, the width $\sigma$ of the beam does not generally exceed 3 mm. On the other hand, when the energy of the beam is reduced, the width $\sigma$ of the beam increases in certain cases up to 12 mm. For areas where the target volume is close to critical organs, it is then necessary to be able to minimize the penumbra of the beam around the target volume.

A device with which the penumbra of a beam of protons or carbon ions delivered on a target according to a dynamic scanning technique may be reduced, is described in document U.S. Pat. No. 7,826,593. The device is as multileaf collimator in which each of the leaves is made in two portions. A first leaf portion is made in a high density material selected from tungsten, osmium and iridium, and is assembled with a second portion made in a more lightweight material such as steel or aluminum. The leaves are positioned along two rows so that said first portions are located facing each other. Although the longitudinal thickness along the axes of the beam of such a collimator is reduced because of the high density of the materials used, the application of such a collimator requires the use of relatively costly materials, some of these materials being difficult to machine or being brittle. The application of such a collimator also requires the development of an assembling method, for example a method for brazing two plates in different materials in order to form a leaf, the joint of which between both plates is of good quality and uniform so that the leaves may slide against each other in order to form an aperture.

The object of the present invention is the possibility of making according to a simpler and less expensive method, a shielding element capable of reducing the penumbra of a hadron beam and having reduced dimensions and weight.

SUMMARY OF THE INVENTION

According to a first aspect, the present invention relates to a method for obtaining a shielding element 1 in order to minimize the penumbra of a hadron beam 2 outside a target area 4, said hadron beam 2 being guided in a longitudinal direction by an irradiation unit 14, said beam 2 having a width σ, the method comprising steps for:

(i) defining a closed 5 or open 5a contour of said target area 4;

(ii) providing a block 13 having a longitudinal thickness 6 capable of blocking the passage of said beam 2 and having a lateral surface 7c perpendicular to said longitudinal thickness 6;

(iii) forming an aperture 11, 17 with a shape similar to said contour and crossing said longitudinal thickness 6 of said block 13 in order to let through said beam 2, said aperture 11, 17 forming a longitudinal internal surface 7a;

the method being characterized in that it comprises an additional step (iv) for trimming said block 13 so as to form a longitudinal external surface 7b around said longitudinal internal surface 7a, said longitudinal internal 7a and longitudinal external 7b surfaces delimiting a side wall 19.

According to a preferred aspect of the method, said step for trimming said block 13 takes into account the width (σ) of the hadron beam 2 so that said wall 19 has a side thickness everywhere greater than at least once the width σ of the beam.

More preferably, said trimming step takes into account the width (σ) of the hadron beam 2 so that said wall 19 has a side thickness in at least one location 8 of less than five times the width (σ) of the beam 2.

According to an embodiment of the method of the present invention, said trimming step is carried out so that said longitudinal external surface 7b is similar to said longitudinal internal surface 7a.

According to an embodiment of the method of the present invention, the method comprises a step for making a supporting means 16 for attaching said shielding element 1 in said irradiation unit 14.

According to a first embodiment of said supporting means 16, the supporting means is an edge located on said external surface 7b formed during said trimming step.

According to a second embodiment of said supporting means 16, said supporting means 16 is a base made in a low density material and having an aperture larger or equal to said aperture 11 with a similar shape to said contour 5, 5a and crossing said longitudinal thickness 6 of said block (13), so as to let through said beam 2.

According to a second aspect, the present invention relates to a shielding element 1 obtained according to one of the embodiments of the method according to the first aspect of the present invention.

According to a third aspect, the present invention relates to an irradiation unit 14 capable of scanning a hadron beam 2 from a source 3 over a target area 4, said irradiation unit 14 comprising a shielding element 1 according to the second aspect of the present invention, positioned between said source 3 and said target area 4 so as to minimize the penumbra of the beam 2 outside said target area 4.

According to a fourth aspect, the present invention relates to a method for scanning a target area 4 with a beam of hadrons 2 stemming from a source 3, characterized in that a shielding element 1 according to the second aspect of the present invention is placed in an irradiation unit 14, between said source 3 and said target area 4, so as to minimize the penumbra of said beam 2 outside said target area 4.

SHORT DESCRIPTION OF THE FIGURES

Figure 1:
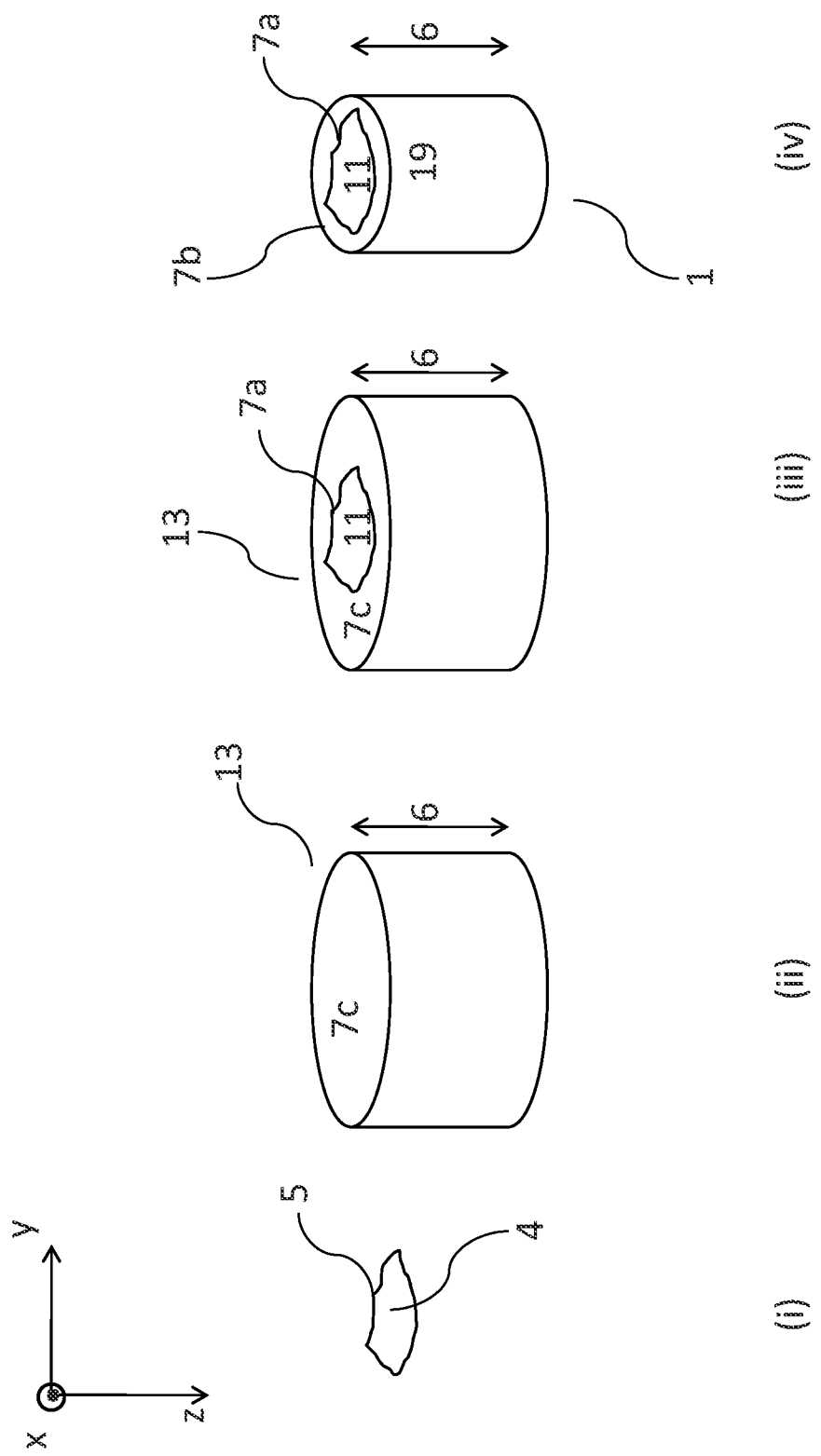
FIG. 1 represents a first embodiment of the method of the first invention.

The figures are given as an indication and do not form a limitation of the present invention, the shielding element according to the present invention preferably having a particular shape depending on the target area to be treated. Moreover, the proportions of the drawings are not observed.

DETAILED DESCRIPTION OF THE INVENTION

According to a first aspect, the present invention relates to a method for obtaining a shielding element 1 for minimizing the penumbra of a hadron beam 2 scanned over a target area 4 outside said target area 4, the hadron beam having a Gaussian width σ, said beam stemming from a source 3 and substantially oriented along an axis z.

In the present case, the term of <<source>> is a point-like location at the origin of the direction taken by the beam 2 after having been deflected by a first scanning means 10 along an axis x and a second scanning means 9 along an axis y, both axes x and y being orthogonal to each other and orthogonal to an axis z parallel to the direction of the beam 2 when the latter is not deflected.

According to a general embodiment of the method of the present invention, the method for obtaining a shielding element 1 comprises the steps for:

(i) defining a closed 5 or open 5a contour of said target area 4;

(ii) providing a block 13 having a longitudinal thickness 6 capable of blocking the passage of the beam 2 and having a lateral surface 7c perpendicular to said longitudinal thickness 6;

(iii) forming an aperture, for example a channel 11 or a concavity 17 crossing said longitudinal thickness 6 of said block 13 for letting through said beam, said aperture being of a shape similar to said contour and forming a longitudinal surface 7a.

The method is characterized in that it comprises an additional step (iv) for trimming said block 13 so as to form a longitudinal external surface 7b around said longitudinal surface 7a, said longitudinal internal 7a and external longitudinal 7b surfaces delimiting a wall 19.

The term of <<longitudinal thickness>> designates a thickness along said axis z. The term of <<longitudinal surface>> designates a surface parallel to the surface z. The aperture 11, 17 is defined depending on the target area to be treated and is of a profile similar to a contour 5 of the target area 4 or to a portion 5a of a contour 5 of the target area 4. The term of <<closed contour>> used in the present application, designates a line closed on itself and which delimits a target area, the term of <<open contour>> designates an open line which delimits a portion of a target area.

Preferably the block 13 provided for forming the shielding element 1 is made in a material having a sufficiently high stopping power for the beam and not being very activated when the latter is subject to irradiation. A material generally used is brass since it is a good compromise which meets both conditions, is inexpensive and is easy to machine.

FIG. 1 illustrates a first embodiment of the method according to the present invention in which the contour of the target area defined in step (i) is a closed contour 5.

Figure 2:
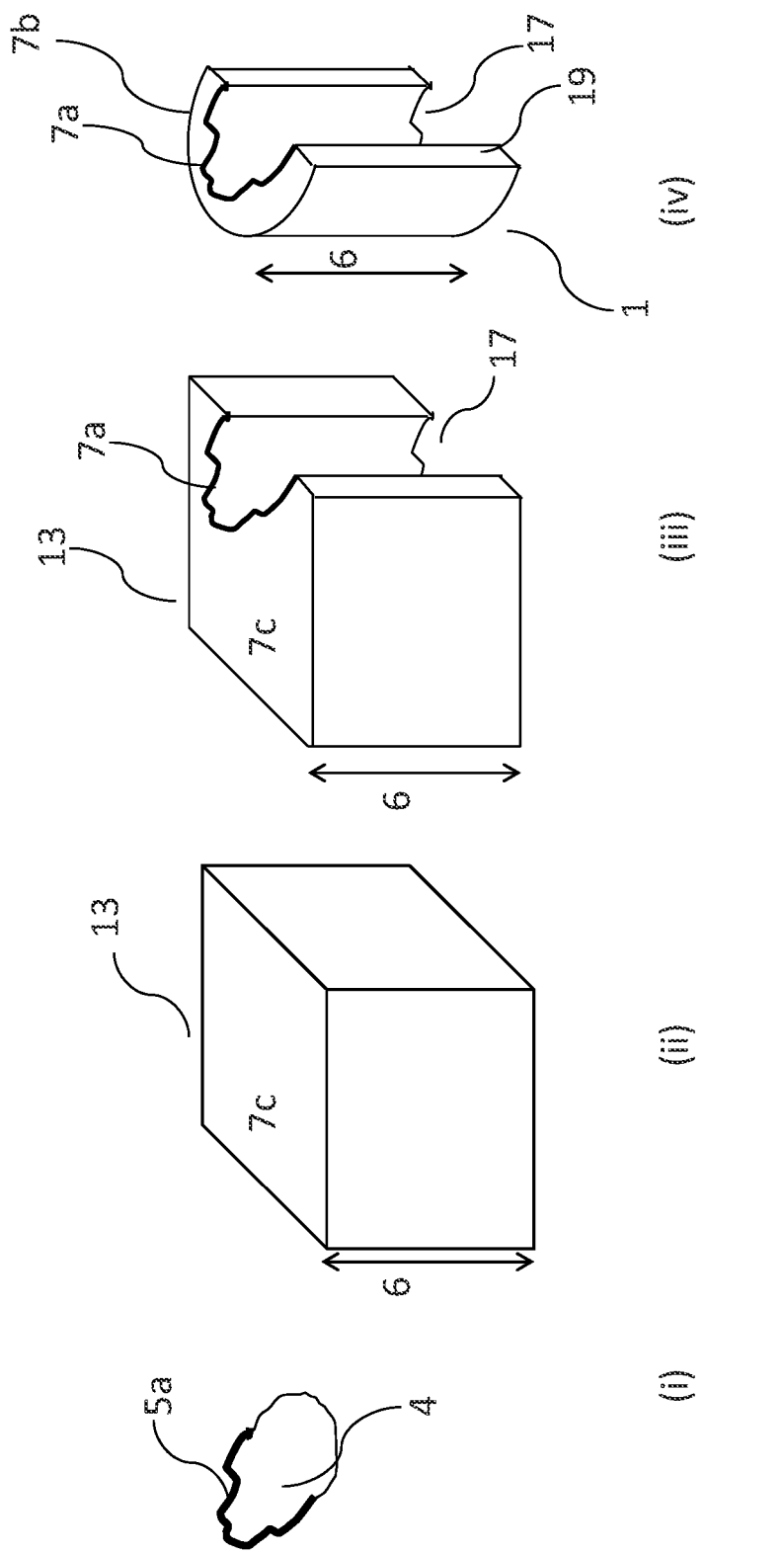
FIG. 2 represents a second embodiment of the method of the present invention.

FIG. 2 represents a second embodiment of the method according to the present invention in which the contour of the target area defined in step (i) is an open contour 5a.

In a third embodiment of the method of the present invention, the method for obtaining the shielding element 1 is characterized in that said trimming step (iv) takes into account the width σ of the hadron beam 2 so that said wall 19 has a side thickness everywhere greater than at least once the width σ of said beam. The term of <<side thickness>> refers to thickness between the longitudinal internal surface 7a and the longitudinal external surface 7b measured in a direction orthogonal to said axis z and perpendicular relatively to the longitudinal internal surface 7a.

For a hadron therapy apparatus using a technique for dynamic scanning of a beam over the target area and comprising a beam energy modulator, the width σ of the beam varies depending on the energy of the beam between a minimum value $\sigma_{min}$ (for example 3 mm) and a maximum value $\sigma_{max}$ (for example 12 mm). In practice, one skilled in the art may choose to carry out said trimming step (iv) so that the side thickness of the side wall is greater than three times the width σ of said beam.

In a fourth embodiment of the method of the present invention, said trimming step takes into account the width σ of the said beam so that said wall 19 has a side thickness everywhere greater than at least once the width σ of said beam and such that said wall 19 has a side thickness in at least one location 8 of less than five times the width σ of said beam.

Figure 3:
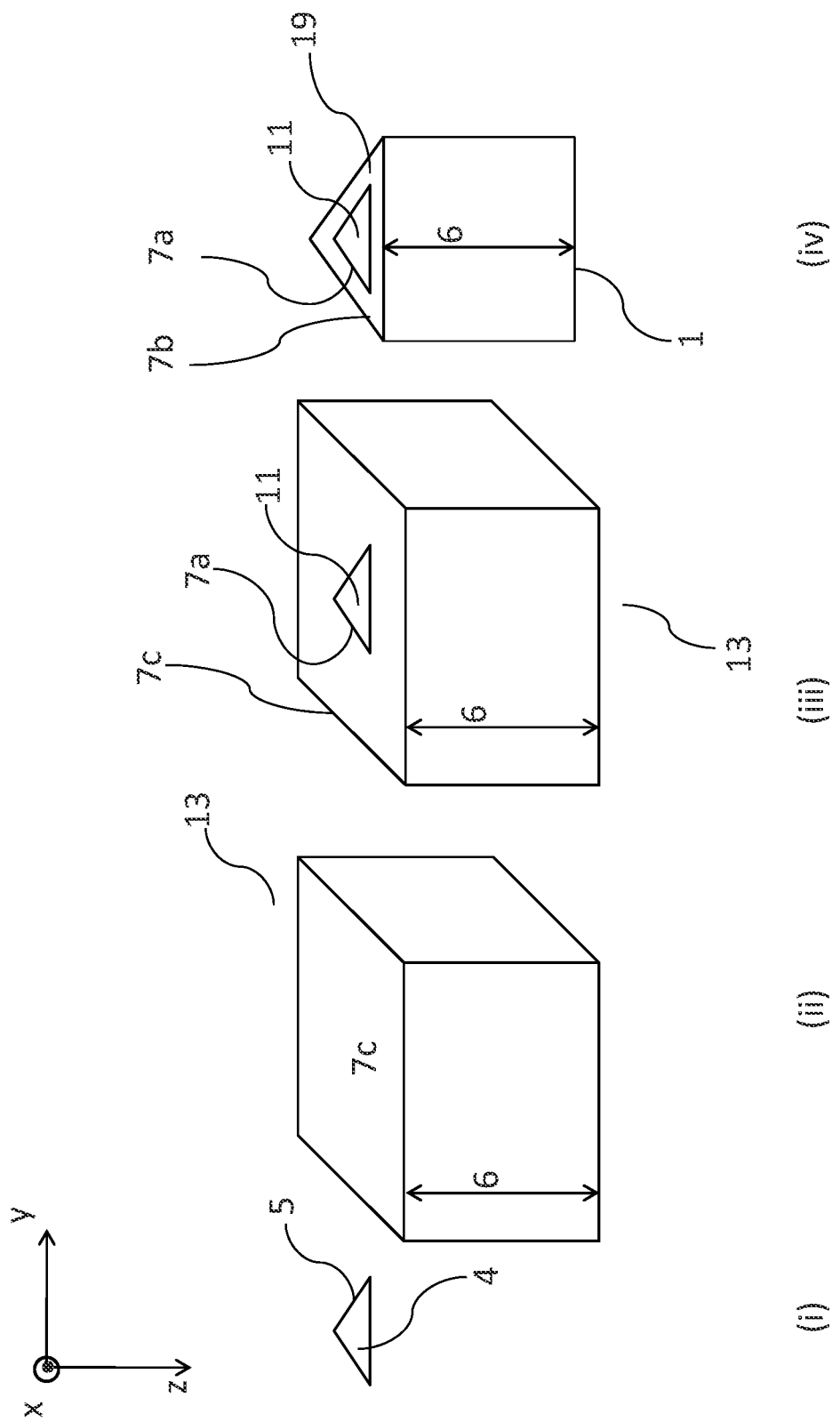
FIG. 3 represents a third embodiment of the method of the present invention.
Figure 4:
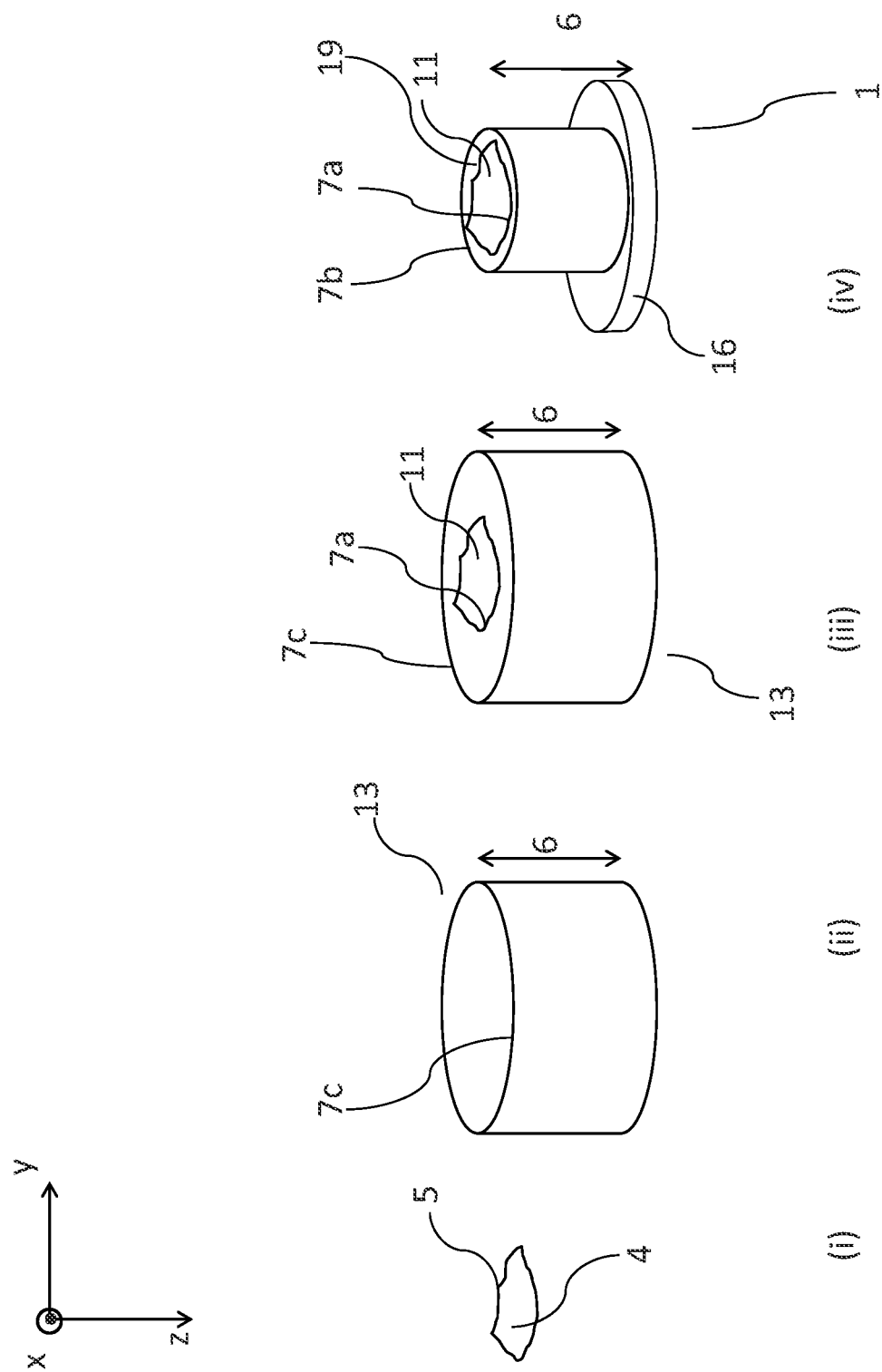
FIG. 4 represents a fourth embodiment of the present invention.

In a fifth embodiment of the method of the present invention as illustrated in FIG. 3, said longitudinal external surface 7b formed during said trimming step is similar to said longitudinal internal surface 7a. Preferably said wall 19 delimited by said longitudinal internal 7a and longitudinal external 7b surfaces has a side thickness everywhere greater than at least once the width σ of the said beam. More preferably, said wall 19 has a side thickness in at least one location 8 of less than five times the width σ of said beam.

Figure 7:
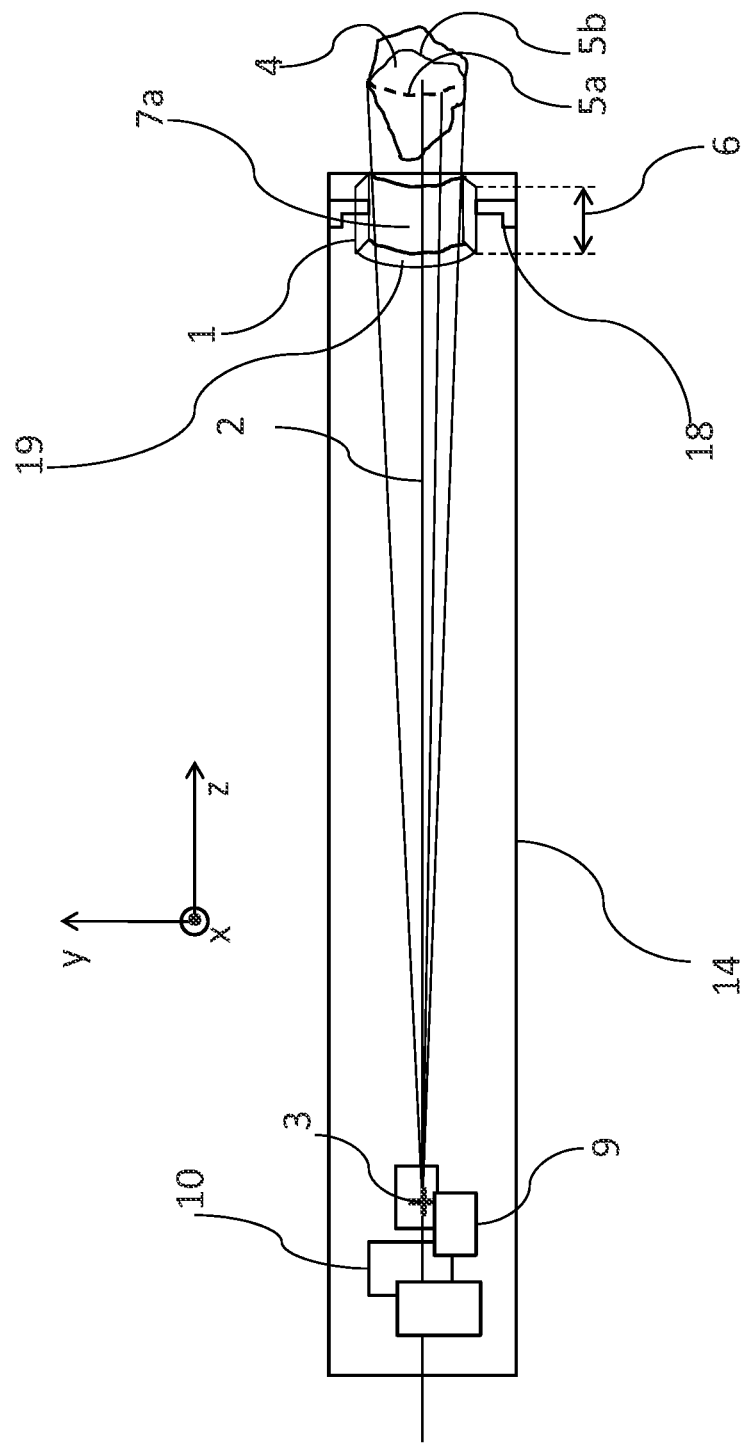
FIG. 7 illustrates an irradiation unit comprising a shielding element according to a second embodiment of the method of the present invention.
Figure 8:
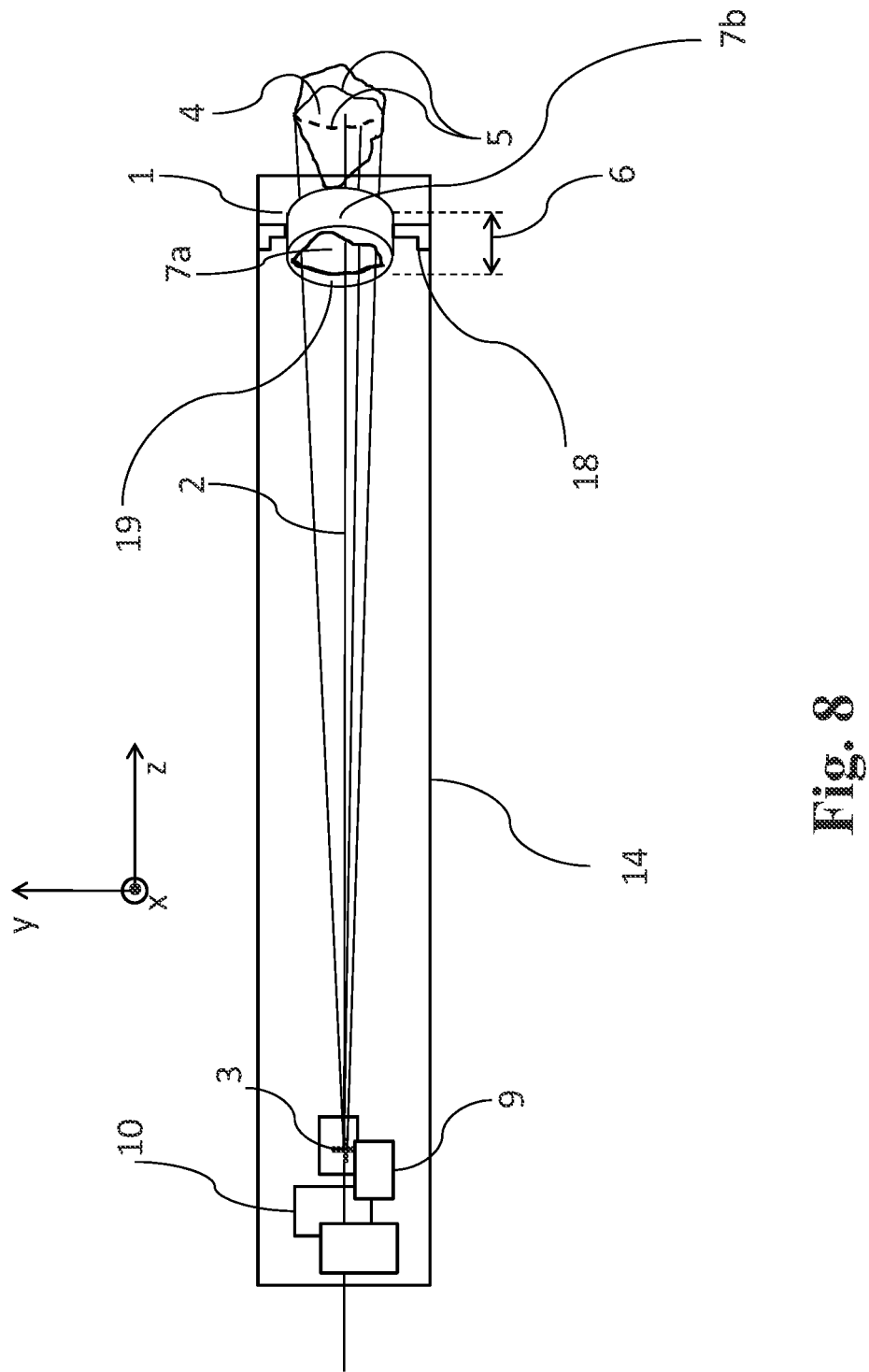
FIG. 8 illustrates an irradiation unit comprising a shielding element according to a first embodiment of the method of the present invention.

In a sixth embodiment of the method according to any of the previous embodiments, said method comprising a step for forming a supporting means 16 for allowing attachment of the shielding element 1 in an irradiation unit 14 as illustrated for example in FIGS. 7 and 8.

According to a first embodiment of the step for forming said supporting means, an edge located on the longitudinal external surface 7b is formed during said trimming step, said edge being used as a supporting means 16. Preferably, said edge is of a size adapted to a device 18 for attaching a shielding element comprised in an irradiation unit 14 as for example illustrated in FIGS. 7 and 8, regardless of the shape of the aperture 11, 17 and of the side thickness of the wall 19.

According to a second embodiment of the step for forming said supporting means 16, a base is attached onto the shielding element 1, said base having an aperture greater than or equal to said aperture 11, 17 formed in said block 13, so as to let through the beam 2. Preferably, the base is of dimensions adapted to a device 18 for attaching a shielding element comprised in an irradiation unit 14 as for example illustrated in FIGS. 7 and 8, regardless of the shape of the aperture 11, 17 and of the side thickness of the wall 19. Preferably, said base is in made in a low density material such as for example plexiglas, which is sufficiently resistant to radiations and sufficiently robust for supporting the weight of the shielding element.

Other methods for forming a supporting means 16 allowing attachment of the shielding element 1 in an irradiation unit 14 may be contemplated by one skilled in the art.

According to a second aspect, the present invention refers to a shielding element 1 obtained by the method of the present invention. FIG. 5a illustrates a view along the axis z of a first embodiment of a shielding element 1 obtained according to the method of the present invention. The shielding element 1 comprises an aperture 17 forming a longitudinal internal surface 7a and around which a longitudinal external surface 7b has been formed by trimming, said longitudinal internal surface 7a delimiting with said longitudinal external surface 7b a side wall 19. Said aperture 17 seen in the xy plane is of a shape similar to an open contour 5a of a target area 4. The side thickness of the wall 19 is everywhere greater than or equal to at least once the width σ of the beam. Such a shielding element 1 may be used for irradiation by a dynamic scanning technique of a target area 4, only one side of which is close to a critical area for which minimization of the penumbra of the beam is desired. Preferably, the side thickness of the wall 19 in at least one location is less than N times the width of said beam, the number N being selected by the user and being advantageously comprised between 1 and 5 so that the weight of the shielding element is minimized while having a side wall 19 capable of preventing passage of the beam.

Figure 5B:
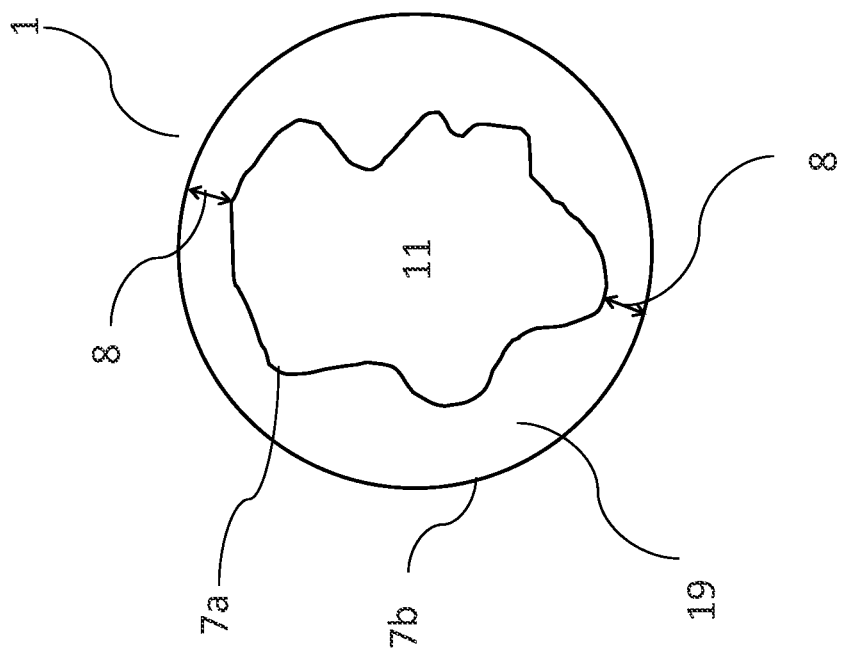
FIG. 5b illustrates a shielding element according to a first embodiment of the method of the present invention.
Figure 5A:
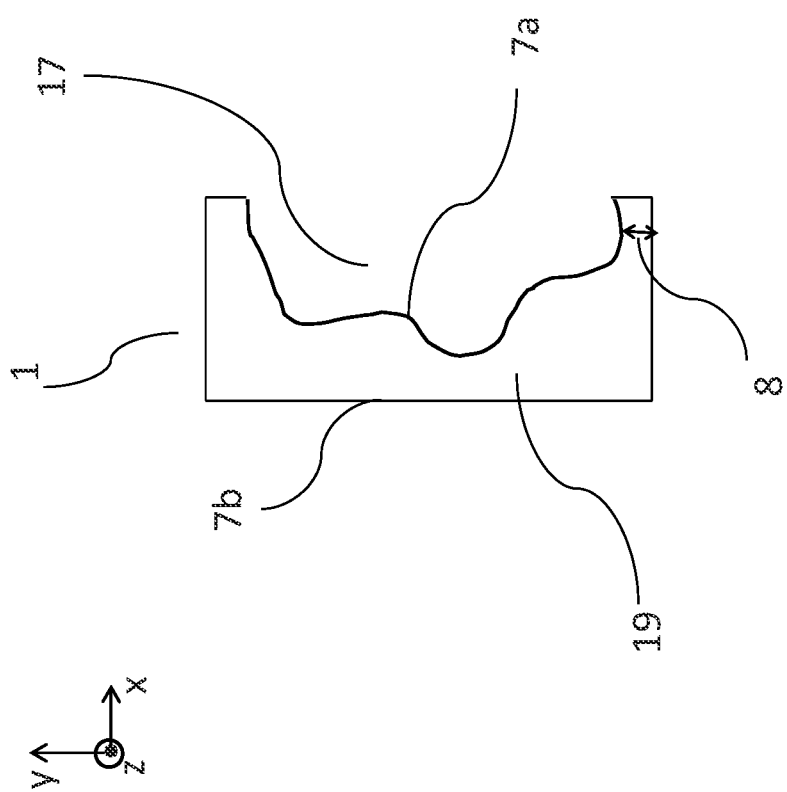
FIG. 5a represents a shielding element according to a second embodiment of the method of the present invention.

FIG. 5b represents a view in the xy plane of a second embodiment of a shielding element 1 obtained according to the method of the present invention. The shielding element 1 comprises an aperture 11 forming a longitudinal internal surface 7a and around which a longitudinal external surface 7b has been formed by trimming, the longitudinal internal surface 7a delimiting with the longitudinal external surface 7b a wall 19. Said aperture 11, seen in the xy plane, is of a shape similar to a closed contour 5 of a target area 4. The side thickness of the wall 19 is everywhere greater than at least once the width σ of the beam. Preferably, the side thickness of the wall 19 in at least one location is less than N times the width σ of said beam, the number N being selected by the user and being advantageously comprised between 1 and 5 so that the weight of the shielding element is minimized while having a wall 19 with dimensions capable of preventing passage of the beam.

Figure 6:
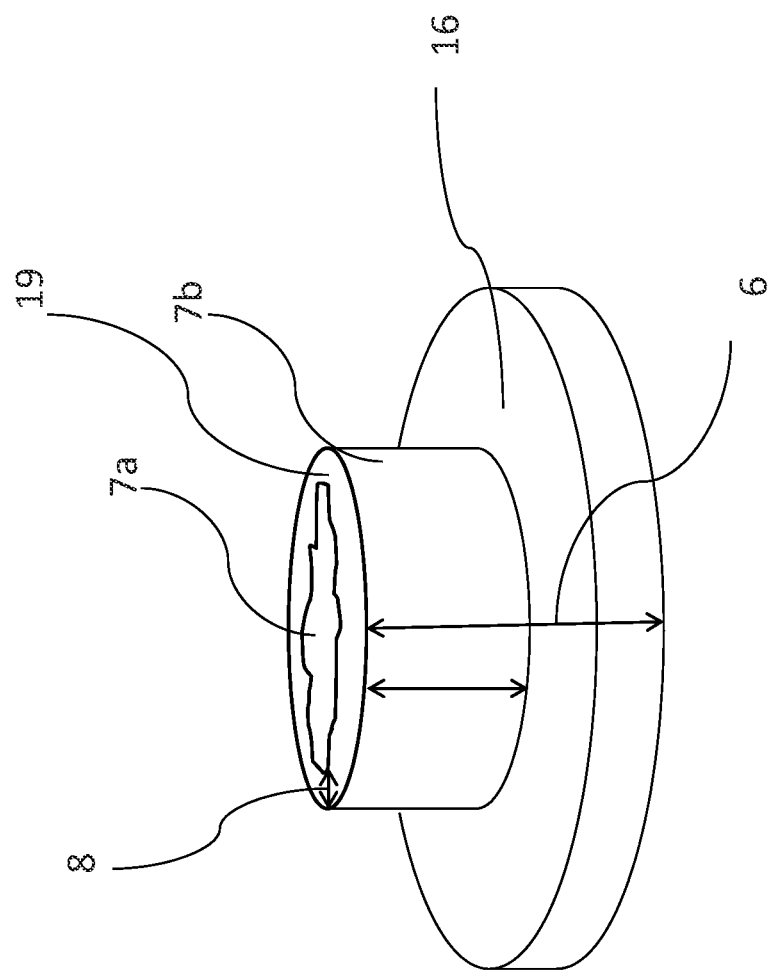
FIG. 6 illustrates a three-dimensional view of a shielding element according to a fourth embodiment of the method of the present invention.

FIG. 6 represents a three-dimensional view of a third embodiment of a shielding element 1 according to the method of the present invention, and comprising a supporting means 16, for example an edge or a base. The shielding element 1 is made in a material with a high stopping power and not being very activated when the latter is subject to irradiation, such as for example brass. When the supporting means 16 is a base, the latter may also be made in the same material as the block 13 which has been used for making the shielding element 1, or in another more lightweight material, as long as the total longitudinal thickness 6 of the shielding element is able to prevent passage of the beam 2.

Each of the shielding elements as described has the advantage of having reduced volume and weight while allowing limitation of the penumbra of a beam of width σ outside the open or closed contour of the target area 4.

According to a third aspect, the present invention relates to an irradiation unit 14 comprising a shielding element 1 according to any of the embodiments described earlier.

Preferably, the irradiation unit 14 is part of a hadron therapy apparatus capable of delivering a beam 2 over a target area 4 according to a dynamic scanning technique. The irradiation unit preferably comprises a first means 10 for scanning the beam along an axis x and a second means 9 for scanning the beam along an axis y, both axes x and y being orthogonal to each other and orthogonal to an axis z parallel to the direction of the beam 2 when the latter is not deflected.

The irradiation unit 14 comprises an attachment means 18 capable of maintaining the shielding element 1 at a distance close to the target area 4 and at a distance away from the source 3. For example, the shielding element 1 is found at a distance of about 2 or 3 meters from the source 3 and at a distance of less than 50 cm from the target area 4.

FIG. 7 illustrates a non-limiting example of the present invention of an irradiation unit 14 comprising a shielding element 1 according to the first embodiment, in which the shielding element 1 comprises an aperture with a shape similar to an open contour 5a of a target area 4.

FIG. 8 illustrates a non-limiting example of the present invention of an irradiation unit 14 comprising a shielding element 1 according to the second embodiment in which the shielding element 1 comprises an aperture 11 with a shape similar to a closed contour 5 of a target area 4.

The irradiation unit 14 according to the present invention may comprise any other embodiment of a shielding element 1 formed according to the method of the present invention.

Preferably, the irradiation unit 14 comprises at the end facing said target area 4 a retractable portion comprising the shielding element 1. Such a retractable portion allows the shielding element to be brought close to the target area 4 so as to deliver a beam with better accuracy, and to move away the shielding element 1 from the target area 4 when a change in the tilt angle of the irradiation unit is desired. In conventional irradiation units, the retractable portion is generally comprised in an enclosure in the open air comprising a sufficiently robust device for displacing the retractable portion, such as for example a rail. By reducing the weight of the shielding element 1 with respect to the collimators and multileaf collimators of the prior art, it is possible to use a telescopic retractable portion of reduced size allowing vacuum to be maintained in the irradiation unit 14 over a longer distance and a less scattered beam to be obtained.

According to a fourth aspect, the present invention relates to a method for scanning a target area 4 with a hadron beam 2 from a source 3, said target area 4 being delimited by a closed 5 or open 5a contour, the method being characterized in that a shielding element 1 according to any of the embodiments described earlier is placed between said source 3 and said target area 4, so as to minimize the penumbra of the beam outside said target area 4. Although the advantage of conventional scanning methods is the benefit of avoiding having to resort to a shielding element, the scanning method according to the present invention has the advantage of protecting more securely critical organs in the neighborhood of the target area.

The reduced weight of said shielding element facilitates its placement in said irradiation unit. The rotation of the irradiation unit is also facilitated because of the reduction of its moment of inertia.

The invention claimed is:

1. A method for obtaining a shielding element for minimizing the penumbra of a scanning hadron pencil beam outside a target area, said hadron beam being scanned over the target area by an irradiation unit, said beam having a width (σ), the method comprising:
   (i) defining a closed or open contour of said target area;
   (ii) providing a block having a longitudinal thickness configured to block the passage of said hadron pencil beam and having a lateral surface perpendicular to said longitudinal thickness;
   (iii) forming an aperture of a shape similar to said contour of said target area, the aperture extending the length of the longitudinal thickness of said block in order to let through said hadron pencil beam, said aperture forming a longitudinal internal surface; and
   (iv) trimming said block so as to form a longitudinal external surface around said longitudinal internal surface, said longitudinal internal and longitudinal external surfaces delimiting a side wall, the side wall having a side thickness everywhere greater than at least once the width (σ) of the hadron pencil beam, and, in at least one location, less than five times the width (σ) of the hadron pencil beam.

2. The method for obtaining a shielding element according to claim 1, wherein the longitudinal external surface is similar to said longitudinal internal surface.

3. The method for obtaining a shielding element according to claim 1, wherein the method further comprises forming a support configured to attach said shielding element in said irradiation unit.

4. The method for obtaining a shielding element according to claim 3, wherein the support comprises an edge located on said longitudinal external surface formed during said trimming step.

5. The method for obtaining a shielding element according to claim 3, wherein the support comprises a base made in a low density material and having an aperture greater than or equal to said aperture of a shape similar to said contour and crossing said longitudinal thickness of said block, so as to let through said beam.

6. A shielding element obtained according to the method of claim 1.

7. An irradiation unit configured to scan a hadron pencil beam from a source over a target area, said irradiation unit comprising the shielding element according to claim 6, positioned between said source and said target area, so as to minimize the penumbra of the hadron pencil beam outside said target area.

8. A method for scanning a target area with a hadron pencil beam from a source, the method comprising placing the shielding element obtained according to claim 6 in an irradiation unit between said source and said target area, so as to minimize the penumbra of said hadron pencil beam outside said target area.

9. The shielding element obtained according to the method of claim 1, wherein the hadron pencil beam has a width (σ) of from about 3 to about 12 mm when exiting the irradiation unit.

10. The shielding element obtained according to the method of claim 1, wherein the longitudinal external surface is similar to said longitudinal internal surface.

11. A method of scanning a target area with a scanning hadron pencil beam, the method comprising:
  positioning a shielding element between a scanning hadron pencil beam irradiation unit and the tumor target area, the shielding element having a longitudinal thickness configured to block the passage of said scanning hadron pencil beam, the shielding element comprising:
    an aperture of a shape similar to an open or closed contour of said target area, the aperture extending the length of the longitudinal thickness of the shielding element in order to let through said scanning hadron pencil beam, said aperture forming a longitudinal internal surface of the shielding element,
    a longitudinal external surface around said longitudinal internal surface, said longitudinal internal and longitudinal external surfaces delimiting a side wall of the shielding element,
  wherein the side wall has a side thickness everywhere greater than at least once the width ($\sigma$) of the scanning hadron pencil beam, and, in at least one location, less than five times the width ($\sigma$) of the scanning hadron pencil beam.

12. The method of scanning a target area according to claim 11, wherein the scanning hadron pencil beam has a width ($\sigma$) of from about 3 to about 12 mm when exiting the scanning hadron pencil beam irradiation unit.

13. The method of scanning a target area with a scanning hadron pencil beam according to claim 11, wherein the longitudinal external surface is similar to said longitudinal internal surface.

14. A shielding element configured for use with a scanning hadron pencil beam irradiation unit whereby a scanning hadron pencil beam is scanned over a target area, said scanning hadron pencil beam having a width ($\sigma$), the shielding element having a longitudinal thickness configured to block the passage of said scanning hadron pencil beam, the shielding element comprising:
  an aperture of a shape similar to an open or closed contour of said target area, the aperture extending the length of the longitudinal thickness of the shielding element in order to let through said scanning hadron pencil beam, said aperture forming a longitudinal internal surface of the shielding element,
  a longitudinal external surface around said longitudinal internal surface, said longitudinal internal and longitudinal external surfaces delimiting a side wall of the shielding element,
wherein the side wall has a side thickness everywhere greater than at least once the width ($\sigma$) of the scanning hadron pencil beam, and, in at least one location, less than five times the width ($\sigma$) of the scanning hadron pencil beam.

15. The shielding element according to claim 14, wherein the scanning hadron pencil beam has a width ($\sigma$) of from about 3 to about 12 mm when exiting a scanning beam irradiation unit.

16. The shielding element according to claim 14, wherein the longitudinal external surface is similar to said longitudinal internal surface.

* * * * *